United States Patent [19]

Stendahl

[11] Patent Number: 5,674,266
[45] Date of Patent: Oct. 7, 1997

[54] BIPHASIC DEFIBRILLATION ISOLATION CIRCUIT AND METHOD

[75] Inventor: Gary B. Stendahl, Crystal, Minn.

[73] Assignee: SurVivaLink Corporation, Minneapolis, Minn.

[21] Appl. No.: 672,698

[22] Filed: Jun. 27, 1996

[51] Int. Cl.$^6$ ........................................ A61N 1/39
[52] U.S. Cl. ................................... 607/63; 607/5
[58] Field of Search ............................ 607/5, 63

[56] References Cited

U.S. PATENT DOCUMENTS

| | | | |
|---|---|---|---|
| 3,590,322 | 6/1971 | Carr | 607/63 |
| 3,857,398 | 12/1974 | Rubin . | |
| 3,862,636 | 1/1975 | Bell et al. | 607/5 |
| 3,886,950 | 6/1975 | Ukkestad et al. . | |
| 4,610,254 | 9/1986 | Morgan et al. . | |
| 4,619,265 | 10/1986 | Morgan et al. . | |
| 4,823,796 | 4/1989 | Benson . | |
| 5,097,830 | 3/1992 | Eikefjord et al. . | |
| 5,405,361 | 4/1995 | Persson . | |

OTHER PUBLICATIONS

W.A., Tacker, Jr., "Defibrillation of the Heart", Chapter 10, pp. 196–222.

*Primary Examiner*—Scott M. Getzow
*Attorney, Agent, or Firm*—Patterson & Keough, P.A.

[57] ABSTRACT

Apparatus for providing a solid state patient isolator circuit capable of conducting bipolar portions of a biphasic defibrillation pulse when the isolator circuit is ON and further capable of isolating circuitry upstream or downstream of the patient isolator when the isolator circuit is OFF. The apparatus includes series connected solid state switching devices having a resistor ladder connected in parallel therewith to balance voltages across the solid state switching devices when the devices are OFF. The solid state switching devices are selected from among the group of uni-directionally conducting solid state switches and are connected between the intermediate nodes of a four diode bridge having an input node and an output node.

7 Claims, 6 Drawing Sheets

BIPHASIC DEFIBRILLATION ISOLATION CIRCUIT AND METHOD

RELATED APPLICATIONS

The present invention is related to the following co-pending U.S. Patent Applications, all of which are assigned to the assignee of the present invention and all of which are hereby incorporated by reference: Parallel Charging of Mixed Capacitors, filed on even date herewith; High Voltage Phase Selector Switch for Defibrillators, filed on even date herewith; Fast Isolated IGBT Driver for High Voltage Switching Circuit, filed on even date herewith; and High Voltage Series Diode Circuit for Capacitor Charging, filed on even date herewith.

BACKGROUND OF THE INVENTION

1. Field of the Invention

This invention relates to the field of external defibrillators. In particular, the present invention relates to a patient isolation circuit for protecting the patient using a biphasic defibrillator.

2. Description of the Related Art

Cardiac arrest, exposure to high voltage power lines and other trauma to the body can result in heart fibrillation which is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is either unconscious or otherwise unable to communicate. Time is of the essence since studies have shown that the chances for successful resuscitation diminish approximately ten percent per minute.

Commercially available defibrillators such as those available from SurvivaLink Corporation, the assignee of the present application, are currently configured to produce monophasic waveform defibrillation pulses. Monophasic (i.e., single polarity) pulses such as a damped sine waveform and a truncated exponential waveform have been demonstrated to be effective for defibrillation, and meet standards promulgated by the Association for Advancement of Medical Instrumentation (AAMI). Electrical circuits for producing monophasic waveform defibrillation pulses are generally known and disclosed, for example, in the Persson U.S. Pat. No. 5,405,316 which is assigned to the assignee of the present invention and the disclosure of which is herein incorporated by reference.

The efficacy of biphasic waveform pulses (effectively two successive pulses of opposite polarities) has been established for implantable defibrillators. For example, studies conducted on implantable defibrillators have shown that biphasic waveform defibrillation pulses result in a lower defibrillation threshold than monophasic pulses. A variety of theories have been proposed to explain the defibrillation characteristics of biphasic waveform pulses but no definite conclusions have been reached. It is anticipated that the efficacy and advantages of biphasic waveform pulses that have been demonstrated in implantable defibrillators will be demonstrated in external defibrillators as well.

Patient isolation circuits for defibrillators are not new. In known isolation circuits for monophasic defibrillation, solid state switches such as silicon controlled rectifiers (SCRs) or thyristors are used. Such devices are not readily adaptable to biphasic defibrillation since they are only capable of unipolar conduction. Thus, there is a continued need for a patient isolation circuit for biphasic defibrillation.

SUMMARY OF THE INVENTION

The present invention provides a patient isolation circuit for biphasic defibrillation. The output circuit of the present invention includes a pair of isolator circuits and an isolator control circuit operable to selectively couple biphasic high voltage pulses to patient leads, and is further operable to isolate the internal circuitry of the defibrillator. The isolation serves two fundamental purposes. The first is to isolate the patient from high voltages during charging. The second is to isolate the circuitry from damage due to externally generated electrical energy which may appear on the patient leads from sources such as another defibrillation charge from another source. The patient isolator of the present invention utilizes steering diodes in combination with low-cost conventional SCRs to allow bipolar and thus biphasic defibrillation pulse delivery.

DETAILED DESCRIPTION OF THE INVENTION

The present invention will be described in detail below. In order to fully understand the present invention, a brief discussion of the associated circuitry for an external defibrillator will be given first.

Related Circuitry

Figure 1:
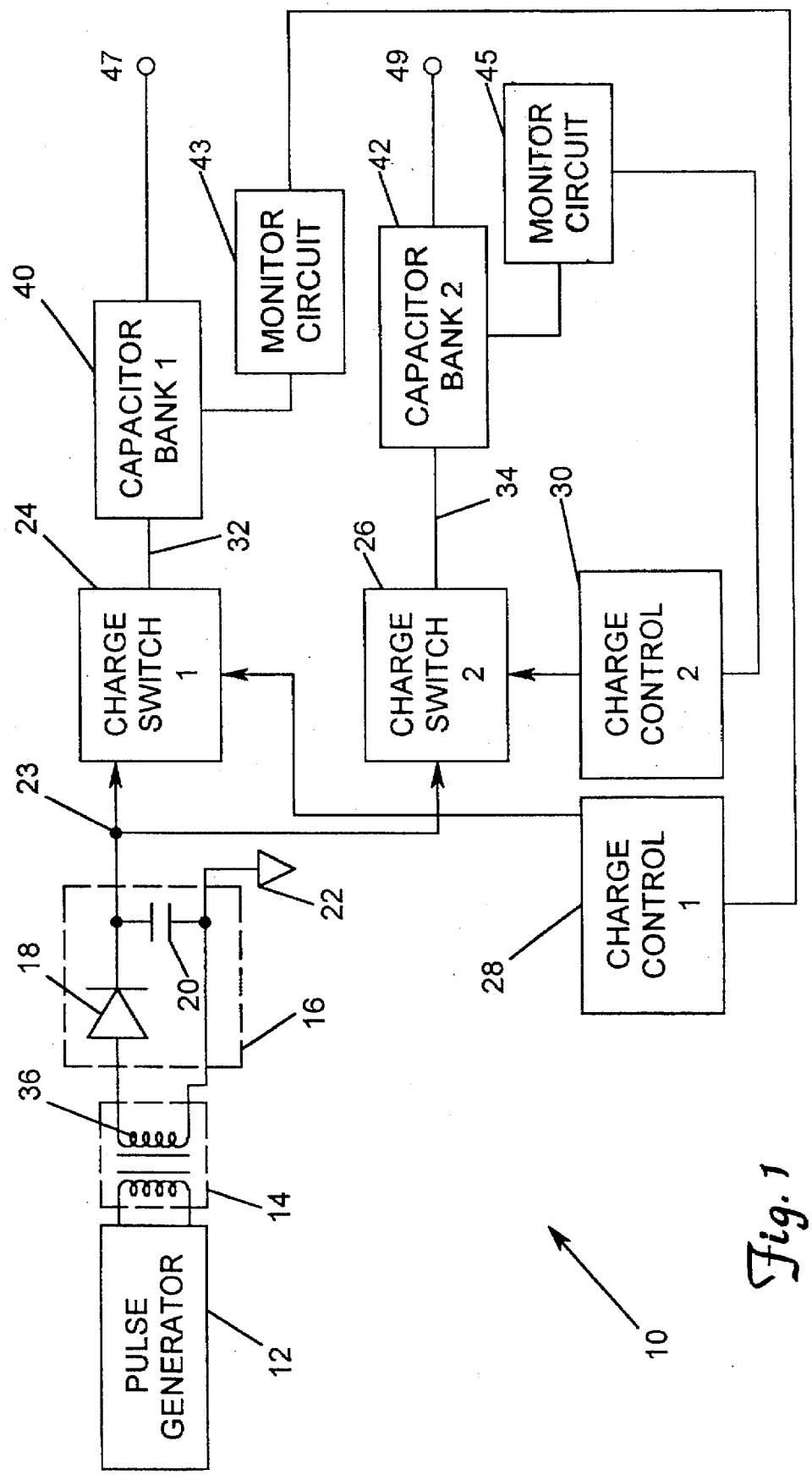
FIG. 1 is a block diagram of a capacitor charge control circuit in accordance with the present invention.

Referring now to FIG. 1, a charge control circuit 10 may be seen. Circuit 10 includes a pulse generator 12 connected to a pulse transformer 14 which is connected to a passive rectifying and filtering circuit 16. Circuit 16 is preferably made up of a high speed (fast recovery) diode 18, which is preferably a UF4007 type, available from General Instruments, and a capacitor 20 which may be in the range of 3–10 microfarads. It should be noted that active filters, as are commonly known, are also equally applicable. Circuit common is indicated by an inverted triangle 22, and an output 23 of the rectifying and filtering circuit 16 is connected to first and second charge switches 24, 26. Charge switches 24, 26 are each preferably formed of one or more solid state switching devices such as a silicon controlled rectifier (SCR), a field effect transistor (FET), or an insulated gate bipolar transistor (IGBT). Such devices may be connected in series (to increase voltage capability) or in parallel (to increase current capability) as is well known in the art. Each of the charge switches 24, 26 is controlled by a separate one of a pair of charge control circuits 28, 30.

The respective outputs 32, 34 of the charge switches 24, 26 are individually connected to one of a pair of capacitor banks 40, 42. Output 32 is connected to a first capacitor bank 40, and output 34 is connected to a second capacitor bank 42. This portion of the circuitry will be described in detail with reference to a pair of capacitor banks but it should be noted that additional capacitor banks may also be included without departing from the spirit or scope of the invention. The output of capacitor bank 40 is connected to an electrode terminal 47 and the output of capacitor bank 42 is connected to an electrode terminal 49.

The circuit is designed to output to electrode terminals 47 and 49 a high voltage defibrillation pulse in the range of approximately 2000–3000 volts in the preferred embodiment. Because the typical impedance values present in external defibrillators is in the range of 25–225 ohms, currents in excess of 100 amps are present. It should be noted however that greater or lesser discharge voltages can also be delivered without departing from the spirit or scope of the invention. In order to generate and deliver the voltage levels desired for defibrillation, a two step process is required. The first step is that of charging the capacitors. The second step is that of discharging the capacitors. To charge low cost, reliable capacitors rapidly to the desired voltage levels, the present invention utilizes charge control circuits 28, 30 and charge switch circuits 24, 26 to charge the capacitors in parallel. When connected in parallel, the total capacitance of a particular capacitance bank is the sum of all the capacitors connected in parallel, while the voltage across each of the individual capacitors is equal. To discharge the capacitors to electrode terminals 47, 49, charge control circuits 28, 30 and charge switch circuits 24, 26 configure the capacitors of a capacitor bank in series. This reduces the total capacitance to a fractional value of the individual capacitors and increase the voltage to the sum of the voltages across each individual capacitor.

The capacitor banks are preferably of differing capacitive values or differing voltage capacities. For example, in one embodiment, capacitor bank 40 has a total capacitance of 7200 microfarads while capacitor bank 42 has a total capacitance of 440 microfarads when connected in parallel for charging. Therefore, capacitor bank 42 will charge much more rapidly than will capacitor bank 40. During discharge, capacitor bank 40 has a total capacitance of 200 microfarads while capacitor bank 42 has a total capacitance of 110 microfarads while connected in series. It should be noted that many other capacitor banks could be utilized having many different capacitance values, or all having the same capacitance value without departing from the spirit or scope of the invention.

The operation of the charge control circuit 10 is as follows. Pulse generator 12 supplies a series, or train, of preferably square wave pulses, typically at a 50% duty cycle and having an amplitude of approximately 400 volts, at a frequency preferably between 5 KHz and 500 KHz. These pulses have a very rapid rise time. Since the fast rise times and high frequencies of the pulses cause avalanching of most common solid state devices of reasonable cost, the pulses are first passed through passive filter circuit 16. Diode 18 is a fast recovery diode that provides for charging of capacitor 20 and prevents discharge of the capacitor 20 through secondary 36 of pulse transformer 14. Capacitor 20 is preferably selected to be able to absorb and store the energy from at least one charge pulse from pulse generator 12.

As stated above, use of a pulse train with a very rapid rise time on individual pulses is desired, but would lead to avalanche breakdown of standard switches if coupled directly thereto. This would cause the switches to lose control of charging, and may lock the switches on, causing the capacitors to be continually charged until they are destroyed. This consequent loss of charging control is unacceptable. Use of rectifying and filtering circuit 16 avoids such avalanche triggering of solid state switches 24, 26 by keeping high dV/dt values from reaching switches 24, 26, allowing ordinary solid state devices to be used for switches 24, 26.

Figure 2:
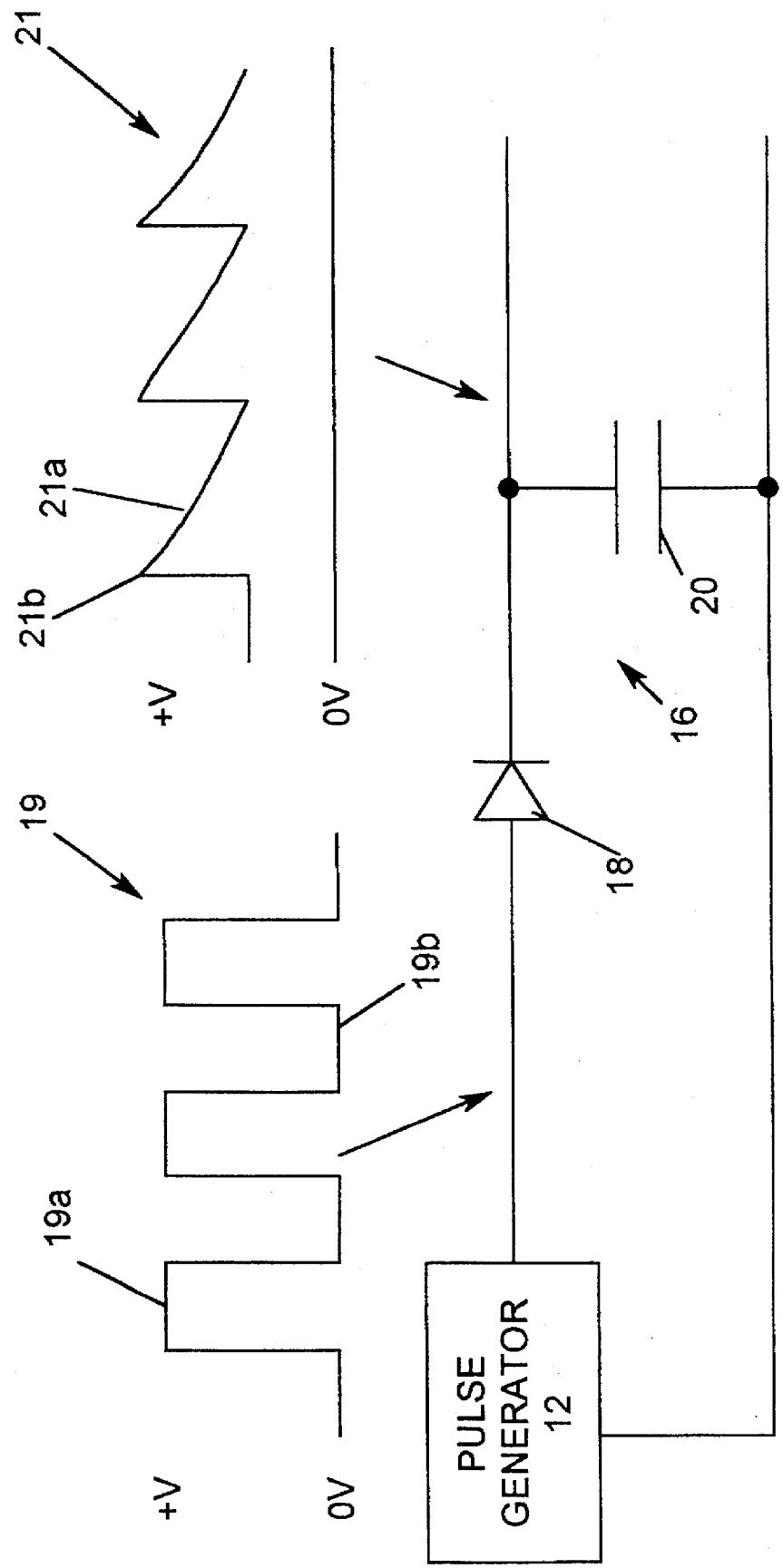
FIG. 2 illustrates a passive filter along with a pictorial representation of a signal before and after the filter.

FIG. 2 illustrates the passive filter along with a pictorial representation of a signal before and after the filter. As can be seen in waveform 19 illustrates the signal coming out of pulse generator 12. This signal is a series of square wave pulses having an amplitude of approximately 400 volts. After passing through filter 16, waveform 21 is obtained which is in the form of a DC level with a generally triangular ripple component. When the ON portion of waveform 19, illustrated at 19a, is seen at diode 18 the diode is forward biased allowing capacitor 20 to charge. Capacitor 20 is charged while diode 18 is forward biased. When signal 19 drops to zero, illustrated at 19b, diode 18 shuts off, halting the charging of capacitor 20. During the off period of diode 18 when the stored energy from capacitor 20 is transferred to the capacitor banks it's voltage drops slightly causing the triangular ripple voltage illustrated in waveform 21 at 21a. After capacitor 20 has a chance to discharge the energy stored therein, diode 18 turns back on due to the presence again of a positive voltage from pulse generator 12 causing waveform 21 to rise to a charged level, at 21b.

The DC charge on capacitor 20 is available to each of switches 24, 26 via lead 23 to be distributed to the capacitor banks as needed. It is to be understood that one or both of switches 24, 26 are on during charging. Both switches 24 and 26 may be on together or only one may be on, but at least one must be on during charging. When one or both of switches 24, 26 is on, the charge on capacitor 20 is coupled to the respective one or both of capacitor banks 40, 42.

As previously stated, the value of capacitor 20 is preferably chosen to be able to absorb and store the energy from one pulse. The energy stored in capacitor 20, which is now in the form of a DC level with a generally triangular ripple component, is available to be delivered to either capacitor bank via charge switches 24 or 26. It is also to be understood that the capacitor banks include slower acting diodes (illustrated as D1 et seq. in FIG. 3 of U.S. Pat. No. 5,405,361, the disclosure of which is hereby incorporated by reference). Thus the pulse provided by transformer 14 is not instantly applied to the capacitors and the energy that is not immediately applied is stored in capacitor 20 and continues to be delivered between pulses from generator 12.

Figure 3:
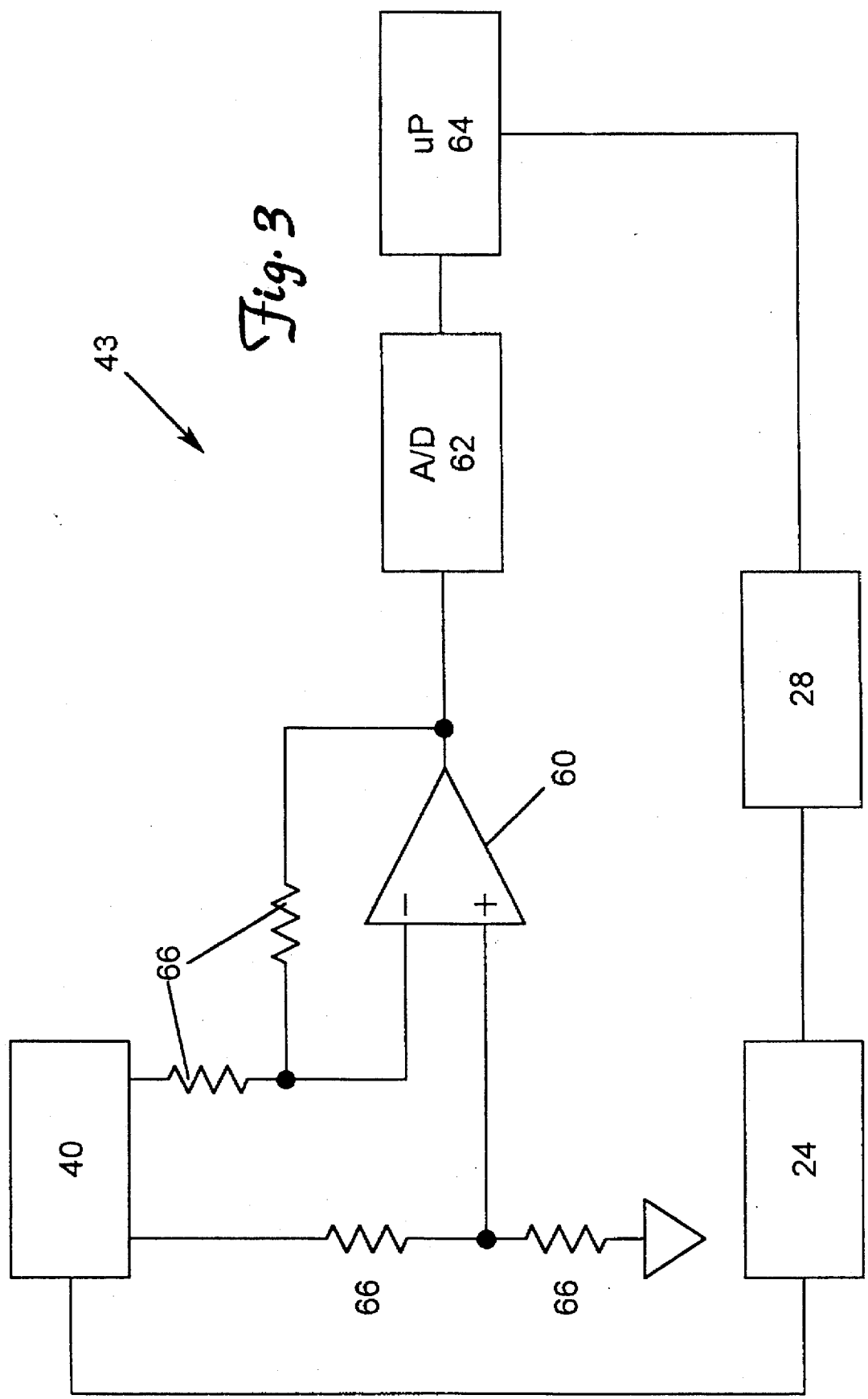
FIG. 3 illustrates one embodiment of a monitoring circuit of the circuit illustrated in FIG. 1.

Circuit 10 also includes voltage monitoring circuits 43, 45 for monitoring the voltage on capacitor banks 40 and 42, respectively. As can be seen in FIG. 1, monitor circuits 43 and 45 are connected to the respective capacitor banks and charge control circuit. Monitoring circuits 43 and 45 are illustrated schematically as block diagrams because there are many different embodiments of monitoring circuits that may be used without departing from the spirit or scope of the invention, such as analog circuitry, digital circuitry and solid state components, for example. FIG. 3 illustrates one preferred embodiment of monitoring circuit 43. It should be noted that monitoring circuit 45 is the same as monitoring circuit 43. As can be seen, an operational amplifier 53 is provided as is an analog to digital converter 55 and a microprocessor 57. Amplifier 60 is connected to capacitor bank 40 via a plurality of resistors 59. In operation, monitoring circuit 43 has a database of preset values stored in microprocessor 57. When capacitor bank 40 reaches the preset value selected in processor 57, charge control circuit 28 is instructed to halt the charging of capacitor bank 40. In an alternative embodiment, microprocessor 57 has the capability of computing an appropriate predetermined value for charging the respective capacitor bank.

When in the charging mode, one or a plurality of capacitor banks may be charged simultaneously. In the embodiment illustrated in FIG. 1 having first and second capacitor banks 40 and 42, if both capacitor banks 40 and 42 are being simultaneously charged, when capacitor bank 42 is fully charged, charge switch 26 is opened as a result of a command from monitoring circuit 45 and all of the charge available at capacitor 20 is then applied to capacitor bank 40 instead of splitting it between the two capacitor banks. When capacitor bank 40 is completely charged, charge switch 24 is opened as a result of a command from monitoring circuit 43. Capacitor banks 40 and 42 are now fully charged and ready to be switched into series for discharge.

Figure 4:
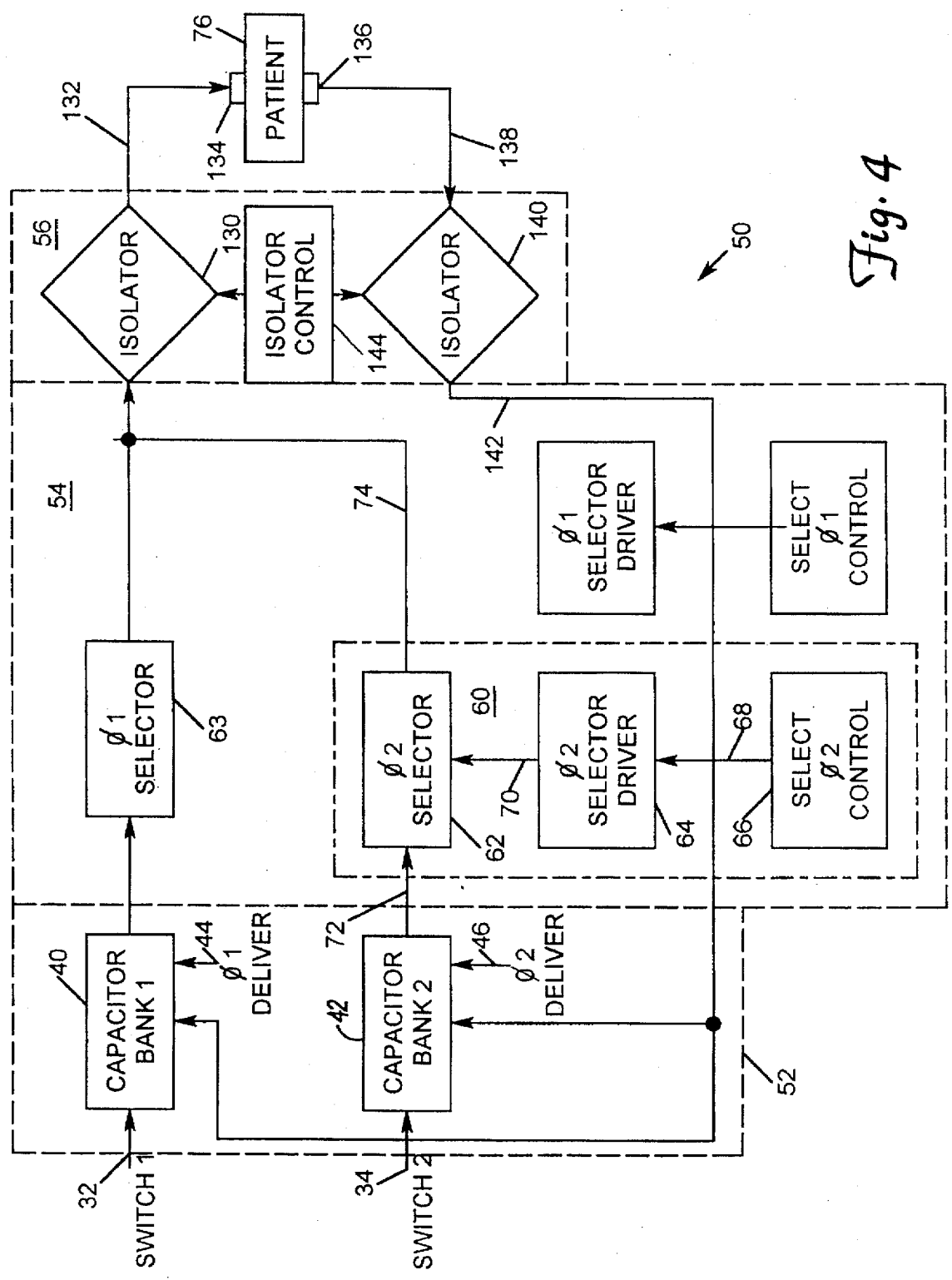
FIG. 4 is a block diagram of a capacitor bank selector and isolation subsystem.

Referring now most particularly to FIG. 4, an output circuit 50 suitable for providing biphasic defibrillation pulses may be seen. Output circuit 50 includes a capacitor bank circuit 52, a selector circuit 54, and an isolator circuit 56. The capacitor bank circuit includes first and second capacitor banks 40, 42, each of which have respective phase delivery command lines 44, 46. In the embodiment illustrated, capacitor bank 40 is configured to discharge a positive first phase of the biphasic output pulse while capacitor bank 42 is configured to discharge a negative second phase. It should be noted that additional capacitor banks can be added without departing from the spirit or scope of the invention. Selector circuit 54 has a pair of preferably identical selector subsystems. One subsystem 60 is indicated by a chain line. Subsystem 60 includes a solid state phase selector switch 62 connected to a phase selector driver 64 which in turn is connected to a select phase control 66. It is to be understood that select phase control 66 provides a signal on line 68 to activate and deactivate phase selector driver 64.

When phase selector driver 64 is activated, it drives phase selector switch 62 to a state of conduction (ON) between lines 72 and 74, connecting capacitor bank 42 to isolator circuit 56 and ultimately to a patient when isolator circuit is itself in a conducting state as will be described infra. When select phase control 66 deactivates phase select driver 64, phase selector switch 62 is rendered nonconductive (OFF) between lines 72 and 74, thus stopping any remainder of the portion of a biphasic defibrillation pulse from being delivered from the capacitor bank 42 to a patient 76. It is to be understood that the phase 1 selector subsystem (connected to capacitor bank 40) is formed of the same elements and operates identically to subsystem 60 in the embodiment shown in FIG. 4. To provide a monophasic defibrillation pulse, only the phase 1 selector subsystem is activated, since capacitor bank 40 is connected to provide a positive polarity output and capacitor bank 42 is connected to provide a negative polarity output.

When providing biphasic defibrillation pulse, it has been found preferable to proceed according to the following sequence:

1. Turn phase 1 selector switch ON, providing a first, positive polarity, exponentially decaying portion of the pulse.
2. Turn phase 1 selector switch OFF, truncating the first portion of the pulse at a desired point.
3. After a time delay, turn phase 2 selector switch ON, providing a second, negative polarity, exponentially decaying portion of the pulse.
4. Turn phase 2 selector switch OFF, truncating the second portion of the pulse at a desired point.

One important aspect of this embodiment is the reduction of the transition time between phase 1 and phase 2. In known systems utilizing SCRs as switching mechanisms, any charge in the capacitors must be reduced below the level of the holding current for the SCR before a phase shift can occur. This can take up to 10 seconds due to the large amount of charge typically remaining on the capacitors. This is so even though photoflash capacitors are typically utilized due to their rapid discharge. In these known systems, SCR dump circuits are also required which are complicated circuits which require many components for each capacitor in the capacitor bank and which force the device to throw away all current stored in the bank.

In this embodiment, the SCR's have been replaced by IGBT's and photoflash capacitors are no longer needed, allowing cheaper, mass-produced products to be used. The delay of switching between phase 1 and phase 2 depends only on the length of time to shut off phase 1 long enough to allow phase 2 to be energized. This time frame is on the order of microseconds. The discharge of current from either capacitor bank 40, 42 may be halted at any time and is able to do so when voltage levels are in excess of 2000–3000 volts. The discharge of an extremely high voltage phase of opposite polarity is begun within 2–3 microseconds following the truncation of the first phase.

Figure 5:
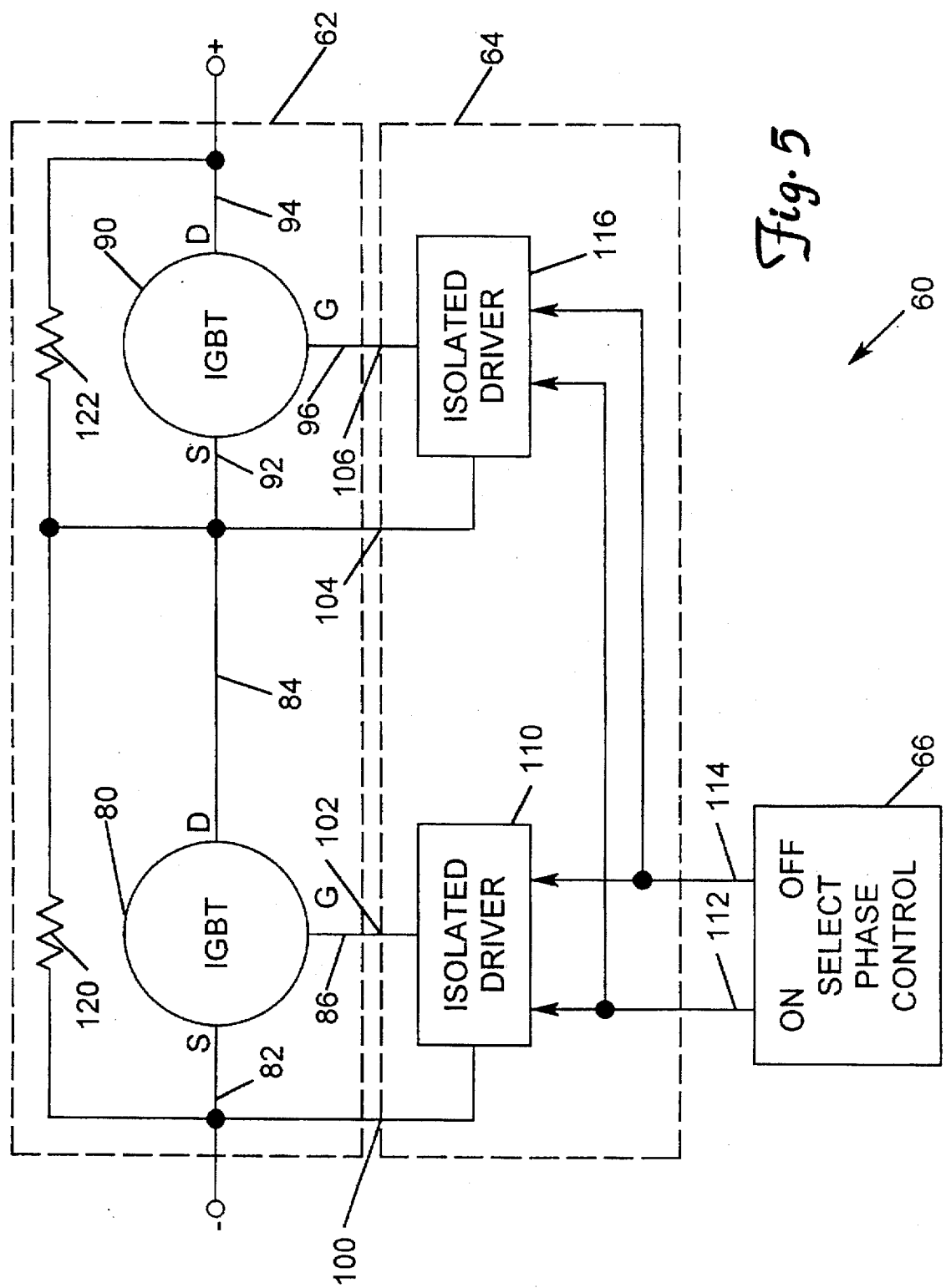
FIG. 5 is a more detailed block diagram of an individual selector, driver and control from FIG. 4.

Referring now also to FIG. 5, details of the phase selector switch 62 may be seen. This embodiment will be described with reference to a pair of IGBT's, but it should be noted that more may be used as will be described below. To withstand the high voltages encountered in providing defibrillation pulses (whether monophasic or biphasic) two IGBT's are connected in series. A first IGBT 80 has a power input 82 and a power output 84 and a signal input or gate 86. Similarly, a second IGBT 90 also has a power input 92, a power output 94, and a signal input, or gate, 96. Referring now also to FIG. 4, power input 82 is connected to lead 72 carrying the output of capacitor bank 42. Power output 84 is connected to power input 92 and power output 94 is connected to lead 74. The connection 70 between phase selector driver 64 and phase selector switch 62 is actually made up of four connections 100, 102, 104, 106. Connections 100 and 102 couple an isolated driver 110 to IGBT 80. Similarly connection 68 between the select phase control 66 and the phase selector driver 64 actually includes two leads 112, 114. As is shown, driver 116 for IGBT 90 (and associated connections) is identical to that described in connection with driver 110. Each of IGBT's 80, 90 is preferably rated to deliver a 360 Joule pulse into a 25 ohm load [at pulse repetition rate of 1 per 5 seconds], and is also preferably rated to withstand 1200 volts in the OFF condition. One such IGBT is type is IXGH25N120A available from IXYS. To prevent unbalanced voltage between IGBT's 80, 90 in the OFF condition, resistors 120, 122 are connected in series with each other and in parallel as a voltage divider across the series connection of IGBT's 80, 90. The resistance of each resistor 120, 122 is preferably 3 mega ohms.

By adding additional IGBT's or by using IGBT's having higher current and voltage limits, the circuit can output each phase successfully at any current or voltage level. Specifically, this allows the switching from phase 1 to phase 2 at voltage levels greater than 1000 volts. For example, by putting four 1200 volt IGBT's in series for each phase, the circuit can withstand (or hold off) 4800 volts per phase or a total of 9600 volts.

The operation of selector subsystem 60 is as follows. When it is desired to turn phase selector switch 62 ON, a low level signal is generated by select phase control 66, providing a logic ON signal on lead 112 and removing a logic OFF signal on lead 114. Drivers 110 and 116 may be any type of voltage isolating driver circuits sufficient to meet the speed and voltage requirements of the defibrillator system. Presently, magnetically isolated conventional driver circuits are preferred. When it is time to turn off phase 1, IGBT's 80 and 90 are closed thus halting the output to the patient without dumping the charge through an auxiliary SCR dumping circuit. The same is done for phase 2. During the time that the current flows through the IGBT's, peak currents are all within the safe operating areas.

Because dumping the charge in capacitor banks 40 and 42 is not needed to change phases, any dumping circuitry desired can be constructed from non-high speed components because time is not critical. This greatly reduces the cost of the components required.

Description of the Present Invention

The isolation circuit of the present invention protects in both directions. This is done to protect both the patient and the circuitry of the defibrillator. In one direction, the isolation circuit protects the patient from any leakage current or from large charges accidentally being applied to the patient. In the opposite direction, the isolation circuit prevents the internal circuitry from damage due to externally generated electrical energy which may appear on the electrodes from sources such as another defibrillator.

Figure 6:
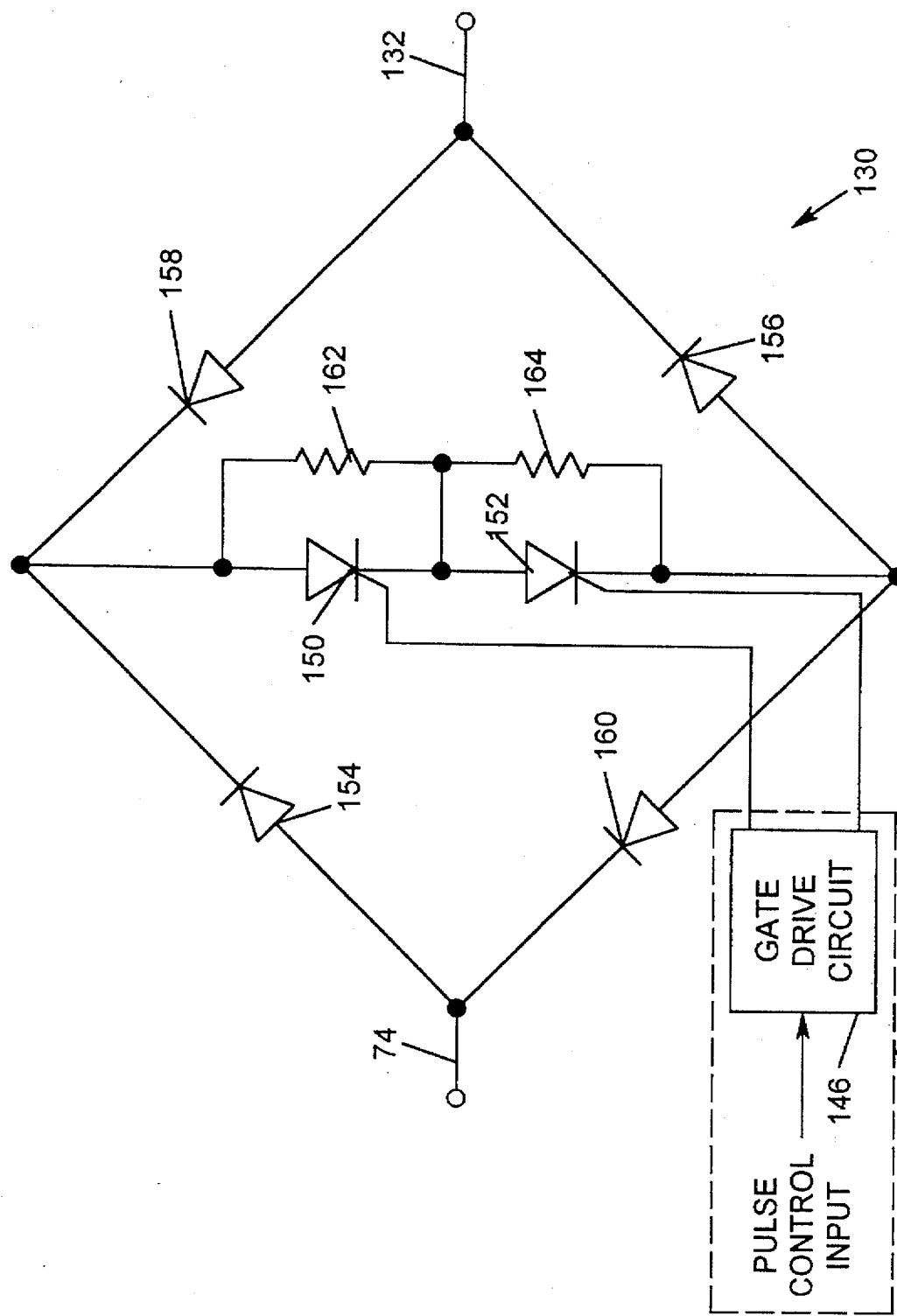
FIG. 6 is a simplified schematic diagram of an isolation circuit according to the present invention.

Referring now most particularly to FIGS. 4 and 6, the output of phase selector switches 62, 63 are combined on lead 74 and connected to a first patient isolator circuit 130. An output 132 of isolator circuit 130 is connected to the patient 76 via a first patient electrode 134. A second patient electrode 136 in contact with the patient is connected to a return line 138 which serves as an input to a second patient isolator circuit 140. An output from isolator circuit 140 on line 142 is connected to both capacitor banks 40, 42 to complete the output defibrillation circuit path. In the embodiment illustrated, patient isolator circuits 130, 140 are preferably identical. The details of each patient isolator circuit 130, 140 are illustrated in FIG. 6, with circuit 130 used as an example.

A single isolator control circuit 144 is connected to both patient isolator circuits 130, 140, with the pulse control input connected to two gate drive circuits, only one of which is shown in FIG. 6. Gate drive circuit 146 may be of conventional design appropriate to isolate and gate a pair of SCRs 150, 152 ON selectively, when commanded by the pulse control input. When ON, SCRs 150, 152 will conduct the positive polarity portion of a biphasic defibrillation pulse through diodes 158, 160. A pair of 3 mega ohm resistors 162, 164 provide voltage balancing between devices 150, 152 when in the OFF condition. Diodes 154, 156, 158, 160 will block conduction between leads 74 and 132 when SCRs 150, 152 are OFF. Furthermore, it is to be understood that the IGBTs in phase selector switches 62, 63 will provide rapid shutoff of the defibrillation pulse, and thus the lack of self commutation in SCRs 150, 152 will not impair system performance by delaying shutoff until the defibrillation pulse current falls below the holding current for the SCRs. It is further to be understood that other solid state devices such as FETs or IGBTs could also be used without departing from the spirit or scope of the present invention.

The invention is not to be taken as limited to all of the details thereof as modifications and variations thereof may be made without departing from the spirit or scope of the invention.

What is claimed is:

1. An external defibrillator high voltage patient isolation circuit for selectively delivering and isolating high voltage biphasic waveform defibrillation pulses, the patient isolation circuit comprising:
   a biphasic pulse generating circuit;
      a diode bridge circuit having diodes connected between an input terminal and an output terminal and having a pair of intermediate terminals, wherein one of the input and output terminals is connected to the biphasic pulse generating circuit and the other of the input and output terminals is adapted for connection to defibrillation electrodes;
      a pair of solid state switching devices connected together in series across the pair of intermediate terminals; and
      a pair of resistors, with each one of the pair of resistors connected across one of the pair of switching devices to balance voltages across the switching devices
   wherein the isolation circuit will provide a high impedance to block biphasic high voltages at either of the input or output terminal from appearing at the other of the input or output terminal when the switching devices are OFF, and a low impedance between the input and output terminals to provide a path for biphasic defibrillation pulses between the biphasic pulse generating circuit and the terminal adapted for connection to defibrillation electrodes when the switching devices are ON.

2. The apparatus of claim 1 wherein the switching devices are SCR's.

3. The apparatus of claim 1 wherein the switching devices are FET's.

4. The apparatus of claim I wherein the switching devices are IGBT's.

5. A method of selectively providing patient isolation in a biphasic external defibrillator comprising the steps of:
   a) providing a diode bridge circuit having diodes connected between an input terminal and an output terminal and having a pair of intermediate terminals;
   b) connecting one of the input and output terminals to a means for providing a source of biphasic high voltage and connecting the other of the input and output terminals to a means for connecting defibrillation pulses to a patient electrode;
   c) connecting at least one unipolar conducting solid state switching device across the pair of intermediate terminals;
   d) turning the solid state switching device ON to establish a biphasic conduction path between the input and the output terminals; and
   e) turning the solid state switching device OFF to block conduction between the input terminal and the output terminal.

6. The method of claim 5 wherein the switching device of step c) further comprises a first device and step c) further comprises connecting a second unipolar conducting solid state switching device in series with the first device across the intermediate terminals and connecting a resistive ladder across the first and second devices to balance the voltages across each of the series connected first and second devices in the OFF condition.

7. The method of claim 5 wherein the switching device is selected from among the group consisting of SCR's, FET's and IGBT's.

* * * * *

UNITED STATES PATENT AND TRADEMARK OFFICE
CERTIFICATE OF CORRECTION

PATENT NO.  : 5,674,266
DATED       : October 7, 1997
INVENTOR(S) : Gary B. Stendahl It is certified that error appears in the above-indentified patent and that said Letters Patent is hereby corrected as shown below:

Column 8, line 33, please change "Claim I" to read "Claim 1".

Signed and Sealed this

Third Day of February, 1998

*Attest:*

BRUCE LEHMAN

*Attesting Officer*     Commissioner of Patents and Trademarks